US006841691B2

(12) United States Patent
Verzijl et al.

(10) Patent No.: US 6,841,691 B2
(45) Date of Patent: Jan. 11, 2005

(54) PROCESS FOR THE PREPARATION OF ENANTIOMERICALLY ENRICHED ESTERS AND ALCOHOLS

(75) Inventors: Gerardus Karel Maria Verzijl, Well (NL); Johannes Gerardus Vries De, Maastricht (NL); Quirinus Bernardus Broxterman, Munstergeleen (NL)

(73) Assignee: DSM N.V., Heerlen (NL)

( * ) Notice: Subject to any disclaimer, the term of this patent is extended or adjusted under 35 U.S.C. 154(b) by 124 days.

(21) Appl. No.: 10/296,840

(22) PCT Filed: May 21, 2001

(86) PCT No.: PCT/NL01/00383

§ 371 (c)(1),
(2), (4) Date: Nov. 26, 2002

(87) PCT Pub. No.: WO01/90396

PCT Pub. Date: Nov. 29, 2001

(65) Prior Publication Data

US 2004/0077059 A1 Apr. 22, 2004

(30) Foreign Application Priority Data

May 26, 2000 (NL) .............................................. 1015313

(51) Int. Cl.$^7$ ................................................. C11G 3/00

(52) U.S. Cl. ..................... 554/167; 554/162; 554/163; 554/170

(58) Field of Search ................................ 554/162, 163, 554/167, 170

(56) References Cited

U.S. PATENT DOCUMENTS

| 5,726,172 | A | 3/1998 | Sparks et al. | ............ 514/230.5 |
| 5,750,549 | A | 5/1998 | Caldwell et al. | ............ 514/364 |
| 5,808,056 | A | 9/1998 | Amato et al. | ................ 540/360 |

FOREIGN PATENT DOCUMENTS

| DE | 4237920 | 11/1992 |
| DE | 4329293 | 3/1995 |
| EP | 0321918 | 6/1989 |
| EP | 314003 | 8/1991 |
| EP | 248414 | 9/1992 |
| EP | 916637 | 5/1999 |
| EP | 360622 | 7/1999 |
| JP | 03236347 | 10/1991 |
| JP | 10245889 | 9/1998 |
| JP | 2000010068 | 1/2000 |
| WO | WO 89/02425 | 3/1989 |
| WO | WO 96/27615 | 9/1996 |
| WO | WO 97/36864 | 10/1997 |
| WO | WO 98/45268 | 10/1998 |
| WO | WO 99/48530 | 9/1999 |

OTHER PUBLICATIONS

Brodfuehrer, P.R. et al., "Asymmetric Synthesis of the Antiarrhythmia Agent d–Sotalol" Org. Process Res. Dec. 1(2):176–178 (1997).
Cohen, N. and Banner, B.L., "Synthesis of 2–Amino–5, 6–dihydro–4H–1,3–thiazines and Related Compounds by Acid Catalyzed Cyclization of Allylic Isothiuonium Salts" J. Heterocycl. Chem. 14(5):717–23 (1977).
Fu, G.C., "From Planarity to Chirality" Chemical Innovation 3–5 (Jan. 2000).
Garrett, C.E. et al., "Nucleophilic Catalysis with π–Bound Nitrogen Heterocycles: Synthesis of the First Ruthenium Catalysts and Comparison of the Reactivity and the Enantioselectivity of Ruthenium and Iron Complexes" J.A. Chem Soc. 120:7479–7483 (1998).
Krämer, R. et al., "Chirale Halbsandwich–Komplexe von Cobalt (III), Rhodium(III), Iridium(III) und Ruthenium(II) Mit Alfa–Aminosäureamid–Glycinnitril– und Peptidester– Liganden" Chemische Berichte, Verlag Chemie GMBH. Weinheim, DE, 126(9):1969–1980 (1993).
Larsson, A. et al., "Enzymatic Resolution of Alcohols Coupled with Ruthenium–Catalyzed Racemization of the Substrate Alcohol" Angew. Chem. Int. Ed. Engl. 36(11):1211–1212 (1997).
Oguni, N. et al., "Enantioselective Addition of Diethylzinc to Arylaldehydes Catalyzed by Chiral Cobalt (II) and Palladium (II) Complexes" Chem. Lett. 6:841–2 (1983).
Palmer, M.J. and Wills, M., "Asymmetric Transfer Hydrogenation of C=and C=N Bonds" Tetrahedron: Asymmetry 10:2045–2061 (1999).
Persson, A., "Ruthenium– and Enzyme–Catalyzed Dynamic Kinetic Resolution F Secondary Alcohols" Journal of the American Chemical Society 121(8):1645–1650 (1999).

*Primary Examiner*—Deborah D. Carr
(74) *Attorney, Agent, or Firm*—Morrison & Foerster LLP

(57) ABSTRACT

Method for the preparation of an enantiomerically enriched ester, in which a mixture of the enantiomers of the corresponding secondary alcohol is subjected, in the presence of an acyl donor, to an enantioselective conversion in the presence of a racemisation catalyst upon which the ester is formed and an acyl donor residue is obtained, and in which the acyl donor residue is irreversibly removed from the phase in which the enantioselective conversion takes place. Preferably the enantioselective conversion is carried out enzymatically and a transfer hydrogenation catalyst is used as racemisation catalyst.

The secondary alcohol can be formed in situ from the corresponding ketone, in the presence of a hydrogen donor. It is also possible to use a mixture of the secondary alcohol and the corresponding ketone as substrate.

Preferably the acyl donor is chosen so that the acyl donor residue is converted in situ into another compound and/or the acyl donor residue is removed via distillation under reduced pressure.

The enantiomerically enriched esters obtained can subsequently be converted into the corresponding enantiomerically enriched alcohols, which are desirable intermediate products in the preparation of liquid crystals, agro chemicals or pharmaceuticals.

19 Claims, No Drawings

PROCESS FOR THE PREPARATION OF ENANTIOMERICALLY ENRICHED ESTERS AND ALCOHOLS

CROSS-REFERENCE TO RELATED APPLICATION

This application is a national phase of PCT application PCT/NL01/00383 filed 21 May 2001, which claims priority from European application 1015313 filed 26 May 2000. The contents of these documents are incorporated herein by reference.

The invention relates to a process for the preparation of an enantiomerically enriched ester, in which a mixture of the enantiomers of the corresponding secondary alcohol is subjected to an enantioselective conversion in the presence of a racemisation catalyst with the aid of an acyl donor upon which the ester is formed and an acyl donor residue is obtained.

Such a process is known for example from Bäckvall, J. A. Chem. Soc. 1999, 121, 1645–1650, in which esters of halogenated phenols are used as acyl donor.

A disadvantage of the known method is that the reaction is carried out at a low concentration. Furthermore the quantity of catalyst that is used is relatively high, and this holds for both the acylation catalyst and the racemisation catalyst. In addition the reaction rate is relatively low. Another disadvantage is that use is made of an acyl donor that is environmentally unfriendly.

The invention now provides a process by which enantiomerically enriched esters can be obtained with a higher yield and a higher production capacity, and in which less acylation and/or racemisation catalyst needs to be used. Furthermore in the process according to the invention use can be made of readily available and inexpensive acyl donors of which the acyl donor residue is not an environmentally unfriendly byproduct.

According to the invention this is achieved in a process wherein the acyl donor residue is irreversibly removed from the phase in which the enantioselective conversion occurs.

The process according to the invention can be carried out in the presence of a ketone.

It has been found that, in contrast to the findings published in Bäckvall, J. A. Chem. Soc. 1999, 121, 1645–1650, the presence of a ketone can have a significant effect on the production capacity, the yield and the reaction rate of the method according to the invention.

The ketone can be chosen in such a way that it corresponds to the alcohol that is used as substrate, or it can be another ketone that is preferably chosen in such a way that it is not also removed from the reaction mixture by the same irreversible method of removal used to remove the acyl donor residue, and that its corresponding alcohol is not acylated by the enzyme. One skilled in the art can simply establish by experimental means which ketones are the most suitable for use in his specific reaction system.

The acyl donor residue is preferably removed from the reaction mixture on a continuous basis, for example by preferentially transferring the acyl donor residue to another phase relative to the acyl donor and the other reaction components. This can be achieved by physical and by chemical methods, or by a combination thereof. Examples of physical methods by which the acyl donor residue can irreversibly be removed from the phase in which the enzymatic reaction occurs, are selective crystallisation, extraction, complexing to an insoluble complex, absorption or adsorption; or by such a choice of the acyl donor that the acyl donor residue is sufficiently volatile relative to the reaction mixture, or is converted in situ into another compound that is sufficiently volatile relative to the reaction mixture to remove the acyl donor residue irreversibly from the reaction mixture; examples of the latter are the application of isopropyl acetate as acyl donor resulting in volatile isopropyl alcohol as acyl donor residue, and the application of isopropenyl acetate as acyl donor, resulting, via isopropenyl alcohol, in volatile acetone as acyl donor residue. In order to remove the acyl donor residue use can be made of a reduced pressure, depending on the boiling point of the reaction mixture. The pressure (at a given temperature) is preferably chosen in such a way that the mixture refluxes or is close to refluxing. In addition it is known to one skilled in the art that the boiling point of a mixture can be lowered by making an azeotropic composition of the mixture. Examples of chemical methods of removal are covalent bonding or chemical or enzymatic derivatization.

Activated forms of carboxylic acids, for example esters or amides or anhydrides, can be used as acyl donor. Examples of suitable acyl donors are esters of $C_1$–$C_{20}$ carboxylic acids, preferably isopropyl acetate, isopropenyl acetate, isobutyl acetate, vinyl acetate, ethyl acetate, isopropyl laureate, isopropenyl laureate or other readily available esters of carboxylic acids and $C_1$–$C_7$ alcohols. Preferably an acyldonor is chosen such that the acyldonor itself is (relatively) not volatile under the reaction conditions while its acyl donor residue is volatile, and oxidation of the substrate is prevented as much as possible under the reaction conditions. Examples of such acyldonors are carboxylic acid esters of an alcohol with 1–4C-atoms and a carboxylic acid with 4–20C-atoms, for instance isopropyl butyric acid ester.

The concentration at which the reaction is carried out is not particularly critical. The reaction can be carried out without a solvent. For practical reasons, for instance when solid or highly viscous reactants or reaction products are involved, a solvent may be used. The reaction can suitably be carried out at higher concentrations, for example at a substrate concentration higher than 0.4 M, in particular higher than 0.8 M. Preferably the substrate (eventually substrate mixture) concentration is higher than 1M, for instance higher than 2M.

The enantioselective conversion of the secondary alcohol in the ester can be carried out with the known asymmetrical acylation catalysts, for example as described in Christine E Garrett et al., J. A. Chem. Soc. 120,(1998) 7479–7483 and references cited therein, and Gregory C. Fu in Chemical innovation/January 2000,3–5. Preferably the enantioselective conversion of the secondary alcohol in the ester is carried out enzymatically.

Suitable enzymes that can be used in the method according to the invention are for example the known enzymes with hydrolytic activity and a high enantioselectivity in such reactions that are also active in an organic environment, for example enzymes with lipase or esterase activity or, when an amide is used as acyl donor, enzymes with amidase activity and esterase or lipase activity, for example originating from *Pseudomonas*, in particular *Pseudomonas fluorescens, Pseudomonas fragi; Burkholderia*, for example *Burkholderia cepacia; Chromobacterium*, in particular *Chromobacterium viscosum; Bacillus*, in particular *Bacillus thermocatenulatus, Bacillus licheniformis; Alcaligenes*, in particular *Alcaligenes faecalis; Aspergillus*, in particular *Aspergillus niger, Candida*, in particular *Candida antarctica, Candida rugosa, Candida lipolytica, Candida cylindracea; Geotrichum*, in particular *Geotrichum candi-* dum; *Humicola*, in particular *Humicola lanuginosa; Penicillium*, in particular *Penicillium cyclopium, Penicillium roquefortii, Penicillium camembertii; Rhizomucor*, in particular *Rhizomucor javanicus, Rhizomucor miehei; Mucor*, in particular *Mucor javanicus; Rhizopus*, in particular *Rhizopus oryzae, Rhizopus arrhizus, Rhizopus delemar, Rhizopus niveus, Rhizopus japonicus, Rhizopus javanicus*; Porcine pancreas lipase, Wheat germ lipase, Bovine pancreas lipase, Pig liver esterase. Preferably an enzyme originating from *Pseudomonas cepacia, Pseudomonas sp., Burkholderia cepacia, Porcine pancreas, Rhizomucor miehei, Humicola lanuginosa, Candida rugosa* or *Candida antarctica* or subtilisin is used. If an R-selective enzyme is used, for example from *Candida antarctica*, the R-ester is obtained as product. Naturally an S-selective enzyme will lead to the S-ester. Such enzymes can be obtained via generally known technologies. Many enzymes are produced on a technical scale and are commercially available. The enzyme preparation as used in the present invention is not limited by purity etc. and can be both a crude enzyme solution and a purified enzyme, but it can also consist of (permeabilised and/or immobilised) cells that have the desired activity, or of a homogenate of cells with such an activity. The enzyme can also be used in an immobilised form or in a chemically modified form. The invention is in no way limited by the form in which the enzyme is used for the present invention. Within the framework of the invention it is of course also possible to use an enzyme originating from a genetically modified microorganism.

Examples of suitable racemisation catalysts are redox catalysts as occurring in transfer hydrogenations. The racemisation catalyst and the acylation catalyst are preferably chosen so that they are mutually compatible, which means that they do not or minimally deactivate each other. The expert can establish by experimental means what acylation/racemisation catalyst combination is suitable for his specific system. The acylation catalyst and/or the racemisation can be used in heterogenised form.

Examples of racemisation catalysts to be chosen are catalysts on the basis of a transition metal compound. Transition metal compounds are described for example in *Comprehensive Organometallic Chemistry 'The synthesis, Reactions and Structures of Organometallic Compounds' Volumes* 1–9, Editor: Sir Geoffrey Wilkinson, FRS, deputy editor: F. Gordon A. Stone, FRS, Executive editor Edward W. Abel, preferably volumes 4, 5, 6 and 8 and in *Comprehensive Organometallic Chemistry 'A review of the literature* 1982–1994', Editor-in-chief: Edward W. Abel, Geoffrey Wilkinson, F. Gordon A. Stone, preferably volume 4 (Scandium, Yttrium, Lanthanides and Actinides, and Titanium Group), volume 7 (Iron, Ruthenium, and Osmium), volume 8 (Cobalt, Rhodium, and Iridium), volume 9 (Nickel, Palladium, and Platinum), volume 11 (Main-group Metal Organometallics in Organic Synthesis) and volume 12 (Transition Metal Organometallics in Organic Synthesis).

As transition metal compound use is preferably made of a transition metal compound of the general formula:

$$M_nX_pS_qL_r$$

where:

n is 1, 2, 3, 4 . . . ;

p, q and r each independently represent 0, 1, 2, 3, 4 . . . ;

M is a transition metal, for example a metal of group 7, 8, 9 or 10 of the periodic system according to the new IUPAC version as shown in the table printed in the cover of the Handbook of Chemistry and Physics, 70th edition, CRC press, 1989–1990, or a lanthanide or a mixture thereof, in particular iron, cobalt, nickel, rhenium, ruthenium, rhodium, iridium, osmium, palladium, platinum or samarium, or a mixture thereof. In the racemisation use is preferably made of palladium, ruthenium, iridium or rhodium, most preferably ruthenium or iridium;

X is an anion such as e.g. hydride, halogenide, carboxylate, alkoxy, hydroxy or tetrafluoroborate;

S is a so-called spectator ligand, a neutral ligand that is difficult to exchange, for example an aromatic compound, an olefin or a diene. Examples of aromatic compounds are: benzene, toluene, xylene, cumene, cymene, naphthalene, anisole, chlorobenzene, indene, cyclopentadienyl derivatives, tetraphenyl cyclopentadienone, dihydroindene, tetrahydronaphthalene, gallic acid, benzoic acid and phenylglycine. It is also possible for the aromatic compound to be covalently bonded to the ligand. Examples of dienes are norbornadiene, 1,5-cyclooctadiene and 1,5-hexadiene.

L is a neutral ligand that is relatively easy to exchange with other ligands and is for example a nitrile or a co-ordinating solvent, in particular acetonitrile, dimethyl sulphoxide (DMSO), methanol, water, tetrahydrofuran, dimethyl formamide, pyridine and N-methylpyrrolidinone.

Examples of suitable transition metal compounds are: $[RuCl_2(\eta^6\text{-benzene})]_2$, $[RuCl_2(\eta^6\text{-cymene})]_2$, $[RuCl_2(\eta^6\text{-mesitylene})]_2$, $[RuCl_2(\eta^6\text{-hexamethlbenzene})]_2$, $[RuCl_2(\eta^6\text{-}1,2,3,4\text{-tetramethylbenzene})]_2$, $[RuCl_2(\eta^6\text{-}1,3,5\text{-triethylbenzene})]_2$, $[RuCl_2(\eta^6\text{-}1,3,5\text{-triisopropylbenzene})]_2$, $[RuCl_2(\eta^6\text{-tetramethylthiophene})]_2$, $[RuCl_2(\eta^6\text{-methoxybenzene})]_2$, $[RuBr_2(\eta^6\text{-benzene})]_2$, $[RuCl_2(\eta^6\text{-benzeen})]_2$, trans-$RuCl_2(DMSO)_4$, $RuCl_2(PPh_3)_3$, $Ru_3(CO)_{12}$, $RU(CO)_3(\eta^4\text{-Ph}_4C_4CO)$, $[Ru_2(CO)_4(\mu\text{-H})(C_4Ph_4COHOCC4Ph_4)]$, $[Ir(COD)_2Cl]$, $[Ir(CO)_2Cl]_n$, $[IrCl(CO)_3]_n$, $[Ir(Acac)(COD)]$, $[Ir(NBD)Cl_2]_2$, $[Ir(COD)(C_6H_6)]^+BF_4^-$, $(CF_3C(O)CHCOCF_3)^-[Ir(COE)_2]^+$, $[Ir(CH_3CN)_4]^+BF_4^-$, $[IrCl_2C_p*]_2$, $[IrCl_2C_p]_2$, $[Rh(C_6H_{10}Cl]_2$ (where $C_6H_{10}$=hexa-1,5-di-ene), $[RhCl_2C_p*]_2$, $[RhCl_2C_p]_2$, $[Rh(COD)Cl]_2$, $CoCl_2$, If necessary the transition metal compound is converted to a transition metal complex by for example exchanging the neutral ligand L with another ligand L', whereby the transition metal compound changes into $M_nX_pS_qL_rL'_i$, or complexing the transition metal compound with a ligand L'. The catalyst on the basis of the transition metal compound and the ligand can be added in the form of separate components of which one is the transition metal compound and the other is the ligand L', or as a complex that contains the transition metal compound and the ligand L'. Suitable racemisation catalysts are obtained for example by complexing the transition metal compound with for example a primary or secondary amine, alcohol, diol, amino alcohol, diamine, mono-acylated diamine, mono-acylated amino alcohol, mono-tosylated diamine, mono-tosylated amino alcohol, amino acid, amino acid amide, amino-thioether, phosphine, bisphosphine, aminophosphine, preferably an aminoalcohol, monoacylated diamine, monotosylated diamine, amino acid, amino acid amide, amino thioether or an aminophosphine. Examples of ligands are described in EP-A-916637 and in Tetrahedron: *Asymmetry* 10 (1999) 2045–2061, complexing not necessarily taking place with the optically active ligand, but optionally with the racemate corresponding to the optically active ligands described. The ligands are preferably used in quantities that vary between 0.5 and 8 equivalents relative to the metal, in particular between 1 and 3 equivalents. In the case of a bidentate ligand use is preferably made of 0.3–8, in particular 0.5–3 equivalents.

An example of a particularly good class of ligands is the class of amino acid amides of the formula (1).

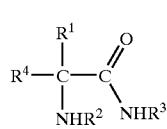

(1)

wherein $R^1$ and $R^4$ each independently represent H or a substituted or unsubstituted alkyl or phenyl group with for instance 1–9 C-atoms; $R^2$ and $R^3$ each independently represent H or a substituted or unsubstituted alkyl group with for instance 1–9 C-atoms, or $R^1$ and $R^2$ form a ring together with the N and C atom to which they are bound.

In most cases activation of catalysts, for example catalysts obtained by complexing of the transition metal compound and the ligand, can be effected for example by treating the transition metal compound or the complex of the transition metal compound and the ligand in a separate step with a base, for example KOH, KOtBu, and subsequently isolating it by removing the base, or by activating the transition metal compound or the complex of the transition metal compound and the ligand in situ, when the acylation/racemisation takes place, with a mild base, for example a heterogeneous base, in particular $KHCO_3$ or $K_2CO_3$, or a homogeneous base, in particular an organic amine, for example triethylamine. It is also possible to activate the transition metal compound with the aid of a reducing agent, for example $H_2$, formic acid and salts thereof, Zn and $NaBH_4$.

The quantities of racemisation catalyst and acylation catalyst to be used are not particularly critical and are for example less than 5, preferably less than 1 mole %, calculated relative to the substrate. The optimum quantities of both catalysts are linked to each other; the quantity of acylation catalyst is preferably adapted so that the overall reaction continues to proceed efficiently, that is to say, that the racemisation reaction does not proceed much slower than the acylation reaction and thus the e.e. of the remaining substrate does not become too high. The optimum ratio between racemisation catalyst and acylation catalyst for a given reaction/catalyst system can simply be established by experimental means.

The secondary alcohol that is used as substrate (substrate alcohol) can if desired be formed beforehand from the corresponding ketone in a separate step (that principally does not need to be stereoselective at all) with the aid of a reducing ancillary reagent, the reduction preferably being catalysed by the racemisation catalyst, and a cheap and preferably volatile alcohol being used as reducing ancillary reagent (non stereoselective transfer hydrogenation).

The substrate alcohol can optionally be formed in situ from the corresponding ketone with the aid of a reducing ancillary reagent. This gives the freedom of choice to employ substrate ketone or substrate alcohol or mixtures of both as substrate. The choice can depend on the availability and the simplicity of the synthesis. If the alcohol is formed in situ from the ketone, a hydrogen donor is also added as ancillary reagent. As ancillary reagent preferably a secondary alcohol is added to the reaction mixture that promotes the conversion of the ketone to the substrate alcohol and is not converted by the acylation catalyst. The ancillary reagent is preferably chosen so that it is not also removed from the reaction mixture by the same irreversible removal method by which the acyl donor residue is removed, that this ancillary reagent is not acylated by the acylation catalyst, and has sufficient reduction potential, relative to the substrate ketone, for the creation of a redox equilibrium. Reducing agents other than alcohols can of course also be used as ancillary reagents. One skilled in the art can simply determine by experimental means which compounds are suitable for use as ancillary reagents in his reaction system.

The product ester obtained may subsequently be isolated from the mother liquor using common practice isolation techniques, depending on the nature of the ester, for instance by extraction, destillation, chromatography or crystallization. If the product is isolated by crystallization further enantiomeric enrichment may be obtained. If desired, the mother liquor (which may contain the alcohol, ester and/or ketone involved in the reaction) may by recirculated to the non stereoselective hydrogenation or to the conversion of the mixture of the enantiomers of the alcohol to the enantiomerically enriched ester. Normally, before recycling the solids will be removed from the mother liquor and, according to common practice, a purge will be built in in order to prevent built up of impurities. If desired, the ester in the mother liquor will first be saponified. This is especially desirable if saponification of the ester under the reaction conditions of the non stereoselective hydrogenation respectively the conversion of the mixture of the enantiomers of the alcohol to the enantiomerically enriched ester, is rather slow.

With the process according to the invention an enantiomerically enriched ester can be obtained with enantiomeric excess (e.e.) larger than 95%, preferably larger than 98%, more preferably larger than 99%, optionally after recrystallization. The enantiomerically enriched ester obtained can subsequently be used as such. If the alcohol is the desired product, the enantiomerically enriched ester is subsequently converted by a known procedure into the corresponding enantiomerically enriched alcohol. This can for example be effected by means of a conversion catalysed by an acid, base or enzyme. When an enantioselective enzyme is used the enantiomeric excess of the product alcohol can be increased further by this. When the enantioselective esterification according to the invention has been carried out with the aid of an enzyme, the same enzyme can very suitably be used for the conversion of the enantiomerically enriched ester into the enantiomerically enriched alcohol. When the ultimate goal is the preparation of the alcohol, the acyl donor can be freely chosen in such a way that the physical or chemical properties of the acyl donor and the acyl donor residue are optimal for the irreversible removal of the acyl donor residue and the treatment of the reaction mixture. With the process according to the invention enantiomerically enriched alcohols with an enantiomeric excess (e.e.) larger than 95%, preferably larger than 98%, more preferably larger than 99% can be obtained, optionally after recrystallization and/or hydrolysis with the aid of an enantioselective enzyme.

The alcohols thus obtained form commonly used building blocks in the preparation of for example liquid crystals, agrochemicals and pharmaceuticals, for example of secondary aliphatic alcohols or aryl alcohols, for example of 1-aryl-ethanols, -propanols, -butanols or -pentanols. In the literature applications are known of for example 1-(4-methoxyphenyl)-2-propenyl-1-ol in J. Heterocycl. Chem (1977), 14 (5), 717–23; 1-(4-methoxyphenyl)-1-propanol in the preparation of liquid crystals and pharmaceuticals (JP-A-01000068); 1-(4-fluorophenyl)-1-ethanol in the preparation of antiarrhytmic agents (d-Sotalol; Org. Process Res. Dec. (1997),1(2),176–178); 1-(2-chlorophenyl)-1-butanol in EP-A-314003; 1-(2,6-difluorophenyl)-1-ethanol in the preparation of antiepileptics (EP-A-248414); 1-(3,5-difluorophenyl)-1-pentanol in the preparation of liquid crystals (WO-A-8902425); 1-(3,4-difluorophenyl)-1-propanol in the preparation of means for the treatment of prostatic hyperplasia and prostatitis (WO-A-9948530); 1-(2-trifluoromethyl-phenyl)-1-ethanol in the preparation of a tocolytic oxytocine receptor antagonist (U.S. Pat. No. 5,726,172); 1-(3-trifluoromethyl-phenyl)-1-ethanol in the preparation of a fungicide (JP-A-10245889); 1-(3,5-bis(trifluoromethyl)-phenyl)-1-ethanol in the preparation of tachykinin receptor antagonist (U.S. Pat. No. 5,750,549); 1-(2-fluor-5-nitro-phenyl)-1-ethanol in the preparation of a herbicide (DE-A-4237920); 1-(3-chloro-4,5-dimethoxyphenyl)-1-ethanol in inhibitors of plasmogen activator inhibitor-1 (WO-A-9736864); 1-methyl-3-(4-acetylphenyl)-1-propanol and 1-methyl-2-(4-acetylphenyl)-1-propanol in the preparation of liquid crystals (EP-A-360622/JP-A-03236347); 4-(1-hydroxyethyl)-benzonitrile in the preparation of nicotine amides as PDE4 D isoenzyme inhibitors (WO-A-9845268); 1-naphthalene-1-ethanol in the separation of enantiomers via HPLC with chiral stationary phase on the basis of polysaccharides (WO-A-9627615); 1-naphthalene-1-propanol as an example of a product in the asymmetrically catalysed dialkyl zinc addition to aldehydes (Chem. Lett. (1983), (6), 841–2); 1-(1,3-benzodioxol-5-yl)-1-butanol in the preparation of a proteinase 3 inhibitor in the treatment of leukemia (U.S. Pat. No. 5,808,056).

The invention also relates to the preparation of an enantiomerically enriched alcohol from the enantiomerically enriched ester obtained.

The invention will be elucidated on the basis of the examples, without however being limited by them.

In all examples the enantioselective transesterification is catalysed by Novozym® 435 (*Candida antartica*). For the tested chiral alcohols the lipase is selective for the R-alcohol. The chiral esters were thus obtained with R-selectivity.

EXAMPLE I AND COMPARATIVE EXPERIMENT A

In a 50-ml Schlenk vessel 8 mmol 1-phenyl ethanol, 16 mmol isopropyl acetate, 0.04 mmol [$Ru_2(CO)_4(\mu$-H)($C_4Ph_4COHOCC_4Ph_4$)] and optionally acetophenone were dissolved under nitrogen in 10 ml toluene. Subsequently 60 mg Novozym® 435 was added to the homogeneous solution. The temperature was increased to 70° C. and the pressure was set. The yields and the e.e.'s were determined after respectively 6 and 23 hours using chiral GC. In the experiments the quantity of acetophenone and the pressure applied were varied (see table).

| Experiment | Pressure (mbar) | Acetophenone (mmol) | T (h) | 1-phenyl ethanol Yield[1] (%) | 1-phenyl ethanol e.e. (%) | 1-phenylethyl acetate Yield[1] (%) | 1-phenylethyl acetate e.e. (%) |
|---|---|---|---|---|---|---|---|
| A | 1000 | 0 | 6 | 52 | 75 | 47 | 99 |
|   |      |   | 23 | 34 | 47 | 63 | 97 |
| I | 220  | 2 | 6 | 25 | 73 | 75 | 98 |
|   |      |   | 23 | 2 | 10 | 99 | 97 |

[1]The yield has been calculated on the quantity of 1-phenyl ethanol used.

EXAMPLE II AND COMPARATIVE EXAMPLE B

In a 50-ml Schlenk vessel 8 mmol 1-phenyl ethanol, 16 mmol isopropenyl acetate, 0.04 mmol [$Ru_2(CO)_4(\mu$-H)($C_4Ph_4COHOCC_4Ph_4$)] and optionally acetophenone were dissolved under nitrogen in 10 ml toluene. Subsequently 60 mg Novozym® 435 was added to the homogeneous solution. The temperature was increased to 70° C. and the pressure was set. The yields and the e.e.'s were determined after respectively 5 and 21 hours using chiral GC. In the experiments the quantity of acetophenone and the pressure applied were varied (see table).

| Experiment | Pressure (mbar) | Acetophenone (mmol) | T (h) | 1-phenyl ethanol Yield[1] (%) | 1-phenyl ethanol e.e. (%) | 1-phenylethyl acetate Yield[1] (%) | 1-phenylethyl acetate e.e. (%) |
|---|---|---|---|---|---|---|---|
| B | 1000 | 0 | 5 | 2 | 78 | 61 | 99 |
|   |      |   | 21 | 0 | — | 62 | 99 |
| II | 200 | 2 | 5 | 26 | 96 | 71 | 99 |
|   |      |   | 21 | 0 | — | 97 | 99 |

[1]The yield has been calculated on the quantity of 1-phenyl ethanol used

COMPARATIVE EXPERIMENT C 2 mmol (R,S)-1-phenyl ethanol and 6 mmol p-chlorophenol acetate were added under nitrogen to 5 ml toluene. Subsequently 0.04 mmol [$Ru_2(CO)_4(\mu$-H)($C_4Ph_4COHOCC_4Ph4$)] was dissolved in the reaction mixture and 60 mg Novozym® 435 was added. The temperature of the reaction mixture was increased to 70° C. The yields and the e.e.'s were determined after 24 hours using chiral GC.
Result:

|  | 1-phenyl ethanol | 1-phenylethyl acetate |
|---|---|---|
| Yield (%) | 1 | 88 |
| e. e. (%) | 11 | 100 |

COMPARATIVE EXPERIMENT D 8 mmol (R,S)-1-phenyl ethanol and 16 mmol p-chlorophenol acetate were added under nitrogen to 10 ml toluene. Subsequently 0.4 mmol [$Ru_2(CO)_4(\mu$-H)($C_4Ph_4COHOCC_4Ph_4$)] was dissolved in the reaction mixture and 60 mg Novozym® 435 was added. The temperature of the reaction mixture was increased to 70° C. The yields and the e.e.'s were determined after 24 hours using chiral GC.
Result:

|  | 1-phenyl ethanol | 1-phenylethyl acetate |
|---|---|---|
| Yield (%) | 32 | 62 |
| e. e. (%) | 46 | 100 |

The results of comparative experiments C and D and of examples I and II are compared in terms of output and yield in the following table.

|      | Output |    |    |    |
|------|--------|----|----|----|
| Exp. | 1)     | 2) | 3) | 4) |
| I    | 0.112  | 22 | 30 | 99 |
| II   | 0.110  | 21 | 30 | 97 |
| C    | 0.051  | 5  | 7  | 88 |
| D    | 0.065  | 14 | 19 | 62 |

1) gramme of ester/gramme of reaction mixture/day
2) gramme of ester/gramme of enzyme
3) gramme of ester/gramme of ruthenium complex
4) chemical yield (mole % relative to substrate)

EXAMPLE III

Concentration Effects

EXAMPLE IIIA

Resolution of (R,S)-1-phenylethanol at 1 M in Toluene

| Placed in a three-necked round bottom flask of 100 ml: | |
|---|---|
| [RuCl$_2$cymene]$_2$ (612.4): | 0.036 mmol |
| (R,S)-α-methyl phenylglycinamide (164): | 0.072 mmol |
| Isopropenyl acetate (100): | 144 mmol |
| (R,S)-1-phenylethanol (122): | 72 mmol |
| toluene: | 48 ml |
| K$_2$CO$_3$ (138) | 3.75 g |

The reaction mixture was degassed by five vacuum/purge cycles with nitrogen. The reaction mixture was stirred at 70° C. for 15 minutes. To the reaction mixture 270 mg Novozym435® was added. At 70° C. the pressure was reduced untill the reaction mixture starts to reflux. While maintaining gentle reflux by adjusting the pressure during the course of the reaction, acetone and a small amount of toluene and isopropenyl acetate was slowly destilled.

EXAMPLE IIIB

Resolution of (R,S)-1-phenylethanol at 2 M in Toluene

| Placed in a three-necked round bottom flask of 100 ml: | |
|---|---|
| [RuCl$_2$cymene]$_2$ (612.4): | 0.036 mmol |
| (R,S)-α-methyl phenylglycinamide (164): | 0.072 mmol |
| Isopropenyl acetate (100): | 144 mmol |
| (R,S)-1-phenylethanol (122): | 72 mmol |
| toluene: | 12 ml |
| K$_2$CO$_3$ (138) | 2.6 g |

The reaction mixture was degassed by five vacuum/purge cycles with nitrogen. The reaction mixture was stirred at 70° C. for 15 minutes. To the reaction mixture 270 mg Novozym435® was added. At 70° C. the pressure was reduced untill the reaction mixture starts to reflux. While maintaining gentle reflux by adjusting the pressure during the course of the reaction, acetone and a small amount of toluene and isopropenyl acetate was slowly destilled.

EXAMPLE IIIC

Resolution of (R,S)-1-phenylethanol without Solvent

| Placed in a three-necked round bottom flask of 100 ml: | |
|---|---|
| [RuCl$_2$cymene]$_2$ (612.4): | 0.036 mmol |
| (R,S)-α-methyl phenylglycinamide (164): | 0.072 mmol |
| Isopropenyl acetate (100): | 72 mmol |
| (R,S)-1-phenylethanol (122): | 72 mmol |
| K$_2$CO$_3$ (138) | 0.4 g |

The reaction mixture was degassed by five vacuum/purge cycles with nitrogen. The reaction mixture was stirred at 70° C. for 15 minutes. To the reaction mixture 270 mg Novozym435® was added. At 70° C. the pressure was reduced untill the reaction mixture starts to reflux. While maintaining gentle reflux by adjusting the pressure during the course of the reaction, acetone and a small amount of isopropenyl acetate was slowly destilled. The isopropenyl acetate was completely destilled after 6 h. To the obtained heterogeneous liquid a second amount of 72 mmol isopropenyl acetate was added and the reaction was continued under slow destillation conditions.

Results

Conversions to R-1-phenethyl acetate were determined by chiral G.C

| Example | t (h) | yield (%) | e.e. (%) | Output (mmol) | (mol/h/l) |
|---|---|---|---|---|---|
| IIIA | 20 | 82 | 99 | 59 | 0.04 |
| IIIB | 20 | 78 | 98 | 56 | 0.08 |
| IIIC | 21 | 70 | 98 | 50.4 | 0.16 |

EXAMPLE IV

Different Phenethanols

General procedure:

| Placed in a three-necked round bottom flask of 100 ml: | |
|---|---|
| [RuCl$_2$cymene]$_2$ (612.4): | 0.018 mmol |
| (R,S)-α-methyl phenylglycinamide (164): | 0.036 mmol |
| Isopropenyl acetate (100): | 72 mmol |
| (R,S)-alcohol: | 36 mmol |
| toluene: | 24 ml |
| K$_2$CO$_3$ (138) | 1.8 g |

The reaction mixture was degassed by five vacuum/purge cycles with nitrogen. The reaction mixture was stirred at 70° C. for 15 minutes. To the reaction mixture 270 mg Novozym435® was added. At 70° C. the pressure was reduced untill the reaction mixture starts to reflux. While maintaining gentle reflux by adjusting the pressure during the course of the reaction, acetone and a small amount of toluene and isopropenyl acetate was slowly destilled.

Results:

| | t | Yield (%) | | | E.e. (%) |
|---|---|---|---|---|---|
| alcohol | (h) | ketone | alcohol | ester | ester |
| (R,S)-1-(4-OCH$_3$-phenyl)-ethanol | 20 | 20 | 1 | 79 | >99 |
| (R,S)-1-(4-Cl-phenyl)-ethanol | 20 | 18 | <1 | 82 | 98 |
| (R,S)-1-(4-Br-phenyl)-ethanol | 20 | 12 | 0 | 88 | 99 |

Conversions to R-acetate were determined by chiral G.C

EXAMPLE V

Resolution of (R,S)-1-phenylethanol Using Isopropylbutyrate as Acylating Agent

Demonstration of a Non Oxidising Procedure

Placed in a three-necked round bottom flask of 100 ml:

| | |
|---|---|
| [RuCl$_2$cymene]$_2$ (612.4): | 0.036 mmol |
| (R,S)-α-methyl phenylglycinamide (164): | 0.072 mmol |
| Isopropyl butyrate (130): | 72 mmol |
| (R,S)-1-phenylethanol (122): | 36 mmol |
| o-xylene: | 24 ml |
| K$_2$CO$_3$ (138) | 3.6 g |

The reaction mixture was degassed by five vacuum/purge cycles with nitrogen. The reaction mixture was stirred at 70° C. for 15 minutes. To the reaction mixture 405 mg Novozym435® was added. At 70° C. the pressure was reduced untill the reaction mixture starts to reflux. While maintaining gentle reflux by adjusting the pressure during the course of the reaction (pressure is slowly decreased from 100 mbar to approximately 70 mbar), isopropanol and a small amount of o-xylene and isopropyl butyrate was slowly destilled.

Result:

Conversions to R-acetate were determined by chiral G.C

| t | Yield (%) | | | E. e. (%) |
|---|---|---|---|---|
| (h) | ketone | alcohol | ester | ester |
| 20 | 0 | <1 | 99 | >99 |

EXAMPLE VI

In a 100-ml three-neck flask 8.1 mmol 1-phenyl ethanol and 2 mmol acetophenone were dissolved under nitrogen in 20 ml isopropyl acetate. 240 mg Novozym® 435 and 0.04 mmol [Ru$_2$(CO)$_4$($\mu$-H) (C$_4$Ph$_4$COHOCC4Ph$_4$)] were added to the solution. The temperature was increased to 70° C. The reaction was continued while solvent was slowly distilled off under reduced pressure. During the reaction the quantity of solvent was controlled by means of fresh isopropyl acetate. The yields and the e.e.'s were determined after 44 hours using chiral GC.

| | acetophenone | 1-phenyl ethanol | 1-phenylethyl acetate |
|---|---|---|---|
| Yield (%) | 11 | 13 | 76 |
| e. e. (%) | — | 90 | 96 |

EXAMPLE VII

Acetophenone (8 mmol), benzhydrol (2 mmol) and isopropyl acetate (16 mmol) were weighed out under nitrogen into a 100-ml three-neck flask. The mixture was dissolved in 15 ml toluene. 60 mg Novozym® 435 and 0.16 mmol [Ru$_2$(CO)$_4$($\mu$-H)(C$_4$Ph$_4$COHOCC$_4$Ph$_4$)] were subsequently added. The reaction mixture was heated to 70° C. and the pressure set to 280 mbar. The yields and the e.e.'s were determined after 29 hours using chiral GC.

Results

| | acetophenone | 1-phenyl ethanol | 1-phenylethyl acetate |
|---|---|---|---|
| Yield (%) | 43 | 2 | 55 |
| e.e. (%) | — | 18 | 100 |

EXAMPLE VIII

A) In a 50-ml Schlenk vessel 8 mmol 1-phenyl ethanol, 2 mmol benzophenone and 16 mmol isopropenyl acetate were added under nitrogen to 10 ml toluene. Subsequently 60 mg Novozym® 435 was added to the homogeneous solution. The temperature was increased to 70° C. and the pressure was set to 200 mbar. After 2 hours (t=0) 0.04 mmol [Ru$_2$(CO)$_4$($\mu$-H) (C$_4$Ph$_4$COHOCC$_4$Ph$_4$)] was dissolved in the reaction mixture. The yields and the e.e.'s were determined after 23 hours using chiral GC.

B) In a 50-ml Schlenk vessel 8 mmol 1-phenyl ethanol, 16 mmol isopropenyl acetate, 0.04 mmol [Ru$_2$(CO)$_4$($\mu$-H) (C$_4$Ph$_4$COHOCC$_4$Ph$_4$)] and 2 mmol acetophenone were dissolved under nitrogen in 10 ml toluene. Subsequently 60 mg Novozym® 435 was added to the homogeneous solution. The temperature was increased to 70° C. and the pressure was set to 200 mbar. The yields and the e.e.'s were determined after 23 hours using chiral GC.

| | | | | 1-phenyl ethanol | | 1-phenylethyl acetate | |
|---|---|---|---|---|---|---|---|
| Experiment | | Acetophenone (mmol) | | Yield[1] (%) | e.e. (%) | Yield[1] (%) | e.e. (%) |
| A | | 14 | | 1 | 100 | 85 | 98 |
| B | | 23 | | 0 | — | 77 | 99 |

EXAMPLE IX

A) In a 50-ml Schlenk vessel 8 mmol 1-phenyl ethanol, 2 mmol benzophenone and 16 mmol isopropenyl acetate were dissolved under nitrogen in 10 ml toluene. Subsequently 60 mg Novozym® 435 was added to the homogeneous solution. The temperature was increased to 70° C. and the pressure was set to 200 mbar. After 2 hours (t=0) 0.04 mmol [Ru$_2$(CO)$_4$($\mu$-H) (C$_4$Ph$_4$COHOCC$_4$Ph$_4$)] was dissolved in the reaction mixture. The yields and the e.e.'s were determined after 23 hours using chiral GC.

B) In a 50-ml Schlenk vessel 8 mmol 1-phenyl ethanol, 16 mmol isopropyl acetate, 0.04 mmol [Ru$_2$(CO)$_4$($\mu$-H)(C$_4$Ph$_4$COHOCC$_4$Ph4)] and optionally 2 mmol acetophenone were dissolved under nitrogen in 10 ml toluene. Subsequently 60 mg Novozym® 435 was added to the homogeneous solution. The temperature was increased to 70° C. and the pressure was set to 220 mbar. The yields and the e.e.'s were determined after 23 hours using chiral GC.

|  |  | 1-phenyl ethanol |  | 1-phenylethyl acetate |  |
|---|---|---|---|---|---|
| Experiment | Acetophenone (mmol) | Yield[1] (%) | e.e. (%) | Yield[1] (%) | e.e. (%) |
| A | 12 | 4 | 49 | 84 | 97 |
| B | 19 | 2 | 10 | 80 | 97 |

EXAMPLE X

In a 250-ml Schlenk vessel 40 mmol 1-phenyl ethanol was dissolved under nitrogen in a mixture of 10 ml isopropyl acetate and 50 ml toluene. Subsequently 300 mg Novozym® 435 was added to the homogeneous solution. The temperature was increased to 70° C. and the pressure was slowly set to 200 mbar. The isopropanol formed was distilled off azeotropically and the filtrate was collected in a continuous extraction system. The isopropanol was extracted continuously to the aqueous phase, the organic phase with the azeotropic composition of toluene/isopropyl acetate being returned to the reaction vessel. After 2 hours (t=0) 0.20 mmol [Ru$_2$(CO)$_4$($\mu$-H)(C$_4$Ph$_4$COHOCC$_4$Ph$_4$)] and 10 mmol acetophenone were added to the reaction mixture. The azeotropic removal of isopropanol was continued at a pressure of approximately 100 mbar. The yields and the e.e.'s were determined after 23 hours using chiral GC.

|  | 1-phenyl ethanol | 1-phenylethyl acetate |
|---|---|---|
| Yield (%)[1] | 21 | 80 |
| e.e. (%) | 89 | 98 |

[1]The yields have not been corrected for the reduction of acetophenone with isopropanol. The yield has been calculated on the basis of the quantity of 1-phenyl ethanol used.

EXAMPLE XI

In a 50-ml Schlenk vessel 8 mmol acetophenone and 0.04 mmol [Ru$_2$(CO)$_4$($\mu$-H) (C$_4$Ph$_4$COHOCC$_4$Ph$_4$)] were dissolved under nitrogen in 10 ml isopropanol. The solution was refluxed for 2 hours at atmospheric pressure. Subsequently the solvent was distilled off under reduced pressure. The residue was dissolved in 10 ml toluene (t=0 hour). Subsequently 16 mmol isopropenyl acetate and 60 mg Novozym® 435 were added to the homogeneous solution. The temperature of the reaction mixture was increased to 70° C. and at 200 mbar solvent was slowly distilled off. At t=18 hours 2.15 mmol 2,4-dimethyl-3-pentanol was added and post-stirring took place for 6 hours at 200 mbar and 70° C. The yields and the e.e.'s were determined at the various points of time using chiral GC.

| time | Acetophenone | 1-phenyl ethanol |  | 1-phenylethyl acetate |  |
|---|---|---|---|---|---|
| (hours) | (%) | Yield (%) | e.e. (%) | Yield (%) | e.e. (%) |
| 0 | 22 | 78 | — | — | — |
| 18 | 22 | 0.6 | 100 | 78 | 99 |
| 24 | 12 | 2.4 | 100 | 86 | 99 |
| 95 | 4 | 1.6 | 24 | 94 | 98 |

EXAMPLE XII

In a 50-ml Schlenk vessel 8 mmol 2-octanol, 2 mmol 2-octanone, 0.8078 mmol mesitylene (internal standard), 20 mmol isopropenyl acetate 0.04 mmol [Ru$_2$(CO)$_4$($\mu$-H)(C$_4$Ph$_4$COHOCC$_4$Ph$_4$)] were dissolved under nitrogen and homogenised in 10 ml toluene. Subsequently 5.3 mg Novozym® 435 was added to the homogeneous solution. The temperature was increased to 70° C. and the pressure was slowly set to 200 mbar. After 23 hours 4 mmol 2,4-dimethyl-3-pentanol was added to the system. The yields and the e.e.'s were determined using chiral GC.

| Time: | 2-octanol |  | 2-octylacetate |  |
|---|---|---|---|---|
| (hours) | Yield (%)[1] | e.e. (%) | Yield (%)[1] | e.e. (%) |
| 5 | 26 | 74 | 50 | 98 |
| 20 | 1 | 35 | 74 | 98 |
| 24 | 3 | 17 | 75 | 98 |
| 45 | 4 | 60 | 90 | 98 |

The yield has been calculated on the quantity of 2-octanol+2-octanone used.

EXAMPLE XIII

In a 50-ml Schlenk vessel 8 mmol 2-octanone, 0.8311 mmol mesitylene (internal standard), 2 mmol isopropanol, 16 mmol isopropyl acetate and 0.04 mmol [Ru$_2$(CO)$_4$($\mu$-H)(C$_4$Ph$_4$COHOCC$_4$Ph$_4$)] were dissolved under nitrogen in 10 ml toluene. Subsequently 30 mg Novozym® 435 was added to the homogeneous solution. The temperature was increased to 70° C. and the pressure set to 300 mbar. The yields and the e.e.'s were determined after 65 hours using chiral GC.

|  | 2-octanone | 2-octanol | 2-octylacetate |
|---|---|---|---|
| Yield (%) | 67 | 1 | 32 |
| e.e. (%) | — | 42 | 97 |

EXAMPLE XIV

In a 50-ml Schlenk vessel 8 mmol acetophenone, 2 mmol isopropanol, 16 mmol isopropyl acetate and 0.04 mmol [Ru$_2$(CO)$_4$($\mu$-H) (C$_4$Ph$_4$COHOCC$_4$Ph$_4$)]] were dissolved under nitrogen in 10 ml toluene. Subsequently 60 mg Novozym® 435 was added to the homogeneous solution. The temperature was increased to 70° C. and the pressure set to 300 mbar. The yields and the e.e.'s were determined after 65 hours using chiral GC.

|  | Acetophenone | 1-phenyl ethanol | 1-phenylethyl acetate |
|---|---|---|---|
| Yield (%) | 42 | 1 | 58 |
| e.e. (%) | — | 36 | 100 |

EXAMPLE XV

In a Schlenk-vessel of 50 ml there was dissolved 8.5 mmol 2-octanone, 0.8 179 mmol mesitylene (internal standard), 9.6 mmol 2,4-dimethyl-3-pentanol, 16 mmol isopropenyl acetate and 0.4 mmol. [Ru$_2$(CO)4($\mu$-H)(C4Ph4COHOCC4Ph4)] under nitrogen in 10 ml toluene. Subsequently 60 mg Novozym® 435 was added to the homogeneous solution. The temperature was increased to 70° C. and the pressure slowly set to 250 mbar. After 25 hours the pressure was lowered further to 200 mbar. The yields and the e.e.'s were determined after 24 hours using chiral GC.

| Time: |  | 2-octanol | | 2-octylacetate | |
|---|---|---|---|---|---|
| (hours) | 2-octanone | Yield (%) | e.e. (%) | Yield (%) | e.e. (%) |
| 5 | 48 | 12 | 77 | 37 | 96 |
| 28 | 9 | 1 | 100 | 90 | 96 |
| 45 | 3 | 0 | — | 96 | 96 |

EXAMPLE XVI

In 50-ml Schlenk vessel 8 mmol 2-octanone and 0.04 mmol [Ru$_2$(CO)$_4$($\mu$-H) (C$_4$Ph$_4$COHOCC$_4$Ph$_4$)] were added under nitrogen to 10 ml isopropanol. The solution was stirred for 3 hours at 80° C. Subsequently the solvent was distilled off under reduced pressure and the residue obtained was dissolved in 10 ml toluene. In the toluene solution 0.9127 mmol mesitylene, 1.8 mmol 2-octanone and 16 mmol isopropenyl acetate were successively dissolved. Subsequently 6 mg Novozym® 435 was added to the homogeneous solution. The temperature was increased to 70° C. and the pressure was slowly set to 200 mbar. After approximately 21 hours 10 mmol 2,4-dimethyl-3-pentanol was added to the mixture. The yields and the e.e.'s were determined using chiral GC.

| Time |  | 2-octanol | | 2-octylacetate | |
|---|---|---|---|---|---|
| (hours) | 2-octanone | Yield (%) | e.e. (%) | Yield (%) | e.e. (%) |
| 19 | 27 | 3 | 26 | 70 | 98 |
| 25 | 13 | 11 | 33 | 77 | 98 |
| 42 | 3 | 9 | 64 | 89 | 98 |

EXAMPLE XVII

In a 50-ml Schlenk vessel 8 mmol 1-phenyl ethanol, 2 mmol acetophenone and 16 mmol vinyl acetate were dissolved under nitrogen in 10 ml toluene. Subsequently 60 mg Novozym® 435 was added to the homogeneous solution. The temperature was increased to 70° C. and the pressure set to 230 mbar. After 0.5 hours (t=0) 0.04 mmol [Ru$_2$(CO)$_4$($\mu$-H) (C$_4$Ph$_4$COHOCC$_4$Ph$_4$)] was dissolved in the reaction mixture. The yields and the e.e.'s were determined after 19 hours using chiral GC.

|  | 1-phenyl ethanol | 1-phenylethyl acetate |
|---|---|---|
| Yield (%) | 12 | 65 |
| e.e. (%) | 0 | 99 |

[1] yield calculated on the quantity of 1-phenyl ethanol used

EXAMPLE XVIII

In a 50-ml Schlenk vessel 8 mmol 1-phenyl ethanol, 2 mmol acetophenone, 16 mmol ethyl acetate and 0.04 mmol [Ru$_2$(CO)$_4$($\mu$-H) (C$_4$Ph$_4$COHOCC$_4$Ph$_4$)] were dissolved under nitrogen in -10 ml toluene. Subsequently 60 mg Novozym ®435 was added to the homogeneous solution. The temperature was increased to 70° C. and the pressure set to 220 mbar. After 23 and 30 hours, respectively, again 16 mmol ethyl acetate was added to the reaction mixture. The yields and the e.e.'s were determined using chiral GC.

| Time | 1-phenyl ethanol | | 1-phenylethyl acetate | |
|---|---|---|---|---|
| (hours) | Yield[1] (%) | e.e. (%) | Yield[1] (%) | e.e. (%) |
| 23 | 53 | 1 | 46 | 99 |
| 30 | 15 | 41 | 85 | 99 |
| 47 | 0 | — | 99 | 99 |

[1] yield calculated on the quantity of 1-phenyl ethanol used.

EXAMPLE XIX

In a 50-ml Schlenk vessel 8 mmol 1-phenyl ethanol, 2 mmol benzophenone and 16 mmol isopropenyl acetate of there was dissolved under nitrogen in 10 ml toluene. Subsequently 240 mg Novozym® 435 was added to the homogeneous solution. The temperature was increased to 70° C. and the pressure lowered to reflux. After 1.5 hours (t=0 hours) 0.16 mmol [Ru$_2$(CO)$_4$($\mu$-H) (C$_4$Ph$_4$COHOCC$_4$Ph$_4$)] was dissolved in the reaction mixture. At t=4 and 20 hours, respectively, 8 mmol isopropenyl acetate and 2 mmol benzhydrol were added to the reaction mixture. After 24 hours the reaction mixture was cooled to room temperature. The enzyme was removed from the reaction mixture by means of filtration. The filtrate was evaporated under reduced pressure at 40° C. The product was isolated from the residue thus obtained by means of distillation at 120° C. and 1.6 mbar. The product was collected in two fractions. Yield: 82%.

| Composition: | acetophenone: | 3% |
|---|---|---|
|  | 1-phenyl ethyl ethanol | 1% |
|  | 1-phenyl ethyl acetate | 96% |
| E.e. (%): | 1-phenyl ethyl acetate | 98% |

EXAMPLE XX 1.6 mmol K$_2$CO$_3$ was introduced into a 50-ml Schlenk tube. The K$_2$CO$_3$ was dried under a vacuum of 10 mbar while being heated to 200–300° C. for 15 minutes. After the dry $K_2CO_3$ had been cooled down to room temperature, 0.04 mmol [RuCl$_2$cymene]$_2$ and 0.008 mmol (R,S) methyl phenyl glycimamide were weighed out and added. The mixture was suspended at 70° C. for 15 minutes in a solution of 8 mmol 1-phenyl ethanol and 16 mmol isopropenyl acetate in 10 ml toluene. Subsequently 25 mg Novozym® 435 was added to the heterogeneous mixture and the pressure was slowly reduced to 200 mbar. If necessary the reaction can be corrected during the run with extra isopropenyl acetate. The yields and the e.e.'s were determined after 24 hours using chiral GC.

Result:

|  | 1-phenyl ethanol | 1-phenylethyl acetate |
|---|---|---|
| Yield (%) | 12 | 77 |
| e.e. (%) | 28 | 99 |

EXAMPLE XXI

Conversion of (R,S)-1-phenylethanol Using Ruthenium Complexes of Amino Alcohols as Racemisation Catalyst

| Placed in a three-necked round bottom flask of 100 ml: | |
|---|---|
| [RuCl$_2$cymene]$_2$ (612,4): | 0.12 mmol |
| Ligand: | 0.24 mmol |
| Isopropenyl acetate (100): | 48 mmol |
| (R,S)-1-phenylethanol (122): | 24 mmol |
| toluene: | 30 ml |
| K$_2$CO$_3$ (138) | 1.3 g |

The resulting mixture was degassed by five vacuum/nitrogen purge cycles. The reaction mixture was heated to 70° C. After complexation at 70° C. for 30 minutes, 45 mg Novozym435® was added. At 70° C. the pressure was reduced untill the reaction mixture starts to reflux. While maintaining gentle reflux by adjusting the pressure during the course of the reaction (pressure is slowly decreased from approximately 260 mbar to 220 mbar), acetone and small amounts of toluene and isopropenyl acetate was slowly destilled.

| Conversions were determined by chiral G.C | | | | |
|---|---|---|---|---|
| | t | Yield (%) | | E.e. (%) |
| catalyst | (h) | ketone | alcohol | ester | ester |
| [RuCl$_2$cymene]$_2$/2-amino-2-Phenyl-1-propanol | 22 | 7 | 25 | 68 | 84 |
| [RuCl$_2$cymene]$_2$/1-amino-2-propanol | 24 | 7 | 23 | 70 | 91 |

EXAMPLE XXII

Conversion of (R,S)-1-phenylethanol Using 0.01 mol % of a Iridium Racemisation Catalyst

| Placed in a three-necked round bottom flask of 100 ml: | |
|---|---|
| [IrCl$_2$Cp*] (796.7): | 0.0036 mmol |
| (R,S)-α-methyl phenylglycinamide (164): | 0.0127 mmol |
| Isopropenyl acetate (100): | 144 mmol |
| (R,S)-1-phenylethanol (122): | 72 mmol |
| toluene: | 48 ml |
| K$_2$CO$_3$ (138) | 3.6 g |

The resulting mixture was degassed by five vacuum/nitrogen purge cycles. The reaction mixture was heated to 70° C. After complexation at 70° C. for 30 minutes, 270 mg Novozym435® was added. At 70° C. the pressure was reduced untill the reaction mixture starts to reflux. While maintaining gentle reflux by adjusting the pressure during the course of the reaction, acetone and small amounts of toluene and isopropenyl acetate was slowly destilled.

| Conversion was determined by chiral G. C | | | | | |
|---|---|---|---|---|---|
| t | Yield (%) | | | E. e. (%) | |
| (h) | Ketone | Alcohol | Ester | Alcohol | ester |
| 20 | 8 | 31 | 61 | 44 (S) | 94 (R) |

EXAMPLE XXIII

Conversion of (R,S)-1-phenylethanol Using Different Transfer Hydrogenation Catalysts

| Placed in a three-necked round bottom flask of 100 ml: | |
|---|---|
| Catalyst precursor: | 0.036 mmol |
| Ligand: | 0.072 mmol |
| Isopropyl butyrate (130): | 72 mmol |
| (R,S)-1-phenylethanol (122): | 36 mmol |
| o-xylene: | 23 ml |
| K$_2$CO$_3$ (138) | 2 g |
| Novozym435 ®: | 400 mg |

The resulting mixture was degassed by five vacuum (50 mbar)/nitrogen purge cycles. The reaction mixture was heated to 70° C. During the course of the reaction the pressure was slowly reduced to 70 mbar. Under the chosen conditions isopropanol and small amounts of o-xylene and isopropyl butyrate were destilled during 22 hours.

Results:

Catalyst precursor:

1. [RuCl$_2$cymene]$_2$ (612,4)
2. [IrCl$_2$Cp*] (796,4)

Ligands:

1. (R,S)-α—Me-PG—NH₂ (164)

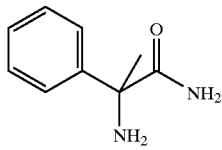

2. (R)-α—Me-PG—NH₂ (164)

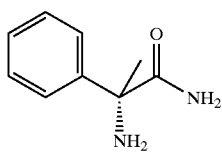

3. (R)-α—Et-PG—NH₂ (178)

4. (R,S))-α—Bn-PG—NH₂ (240)

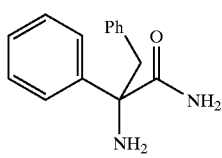

5. (R,S))-α—H-PG—NH₂ (150)

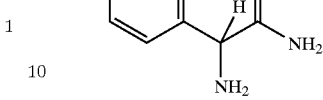

6. (R,S))-α—Me-HHPG—NH₂ (170)

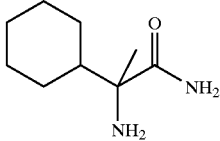

7. (R,S)-IVa—NH₂ (116)

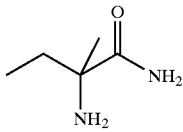

8. (R,S)-α—Me-PG—OH (165)

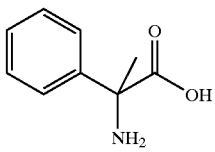

TABLE

Conversion of (R,S)-1-phenylethanol after 22 h using different catalysts

| | Precursor | | | | |
|---|---|---|---|---|---|
| | [RuCl₂cymene]₂ | | | [IrCl₂Cp] | |
| | Yield (%) | | E. e. (%) | Yield (%) | E. e. (%) |
| Ligand | Alcohol | Ester | Ester | Alcohol | Ester | Ester |
| (R,S)-α-Me-PG-NH₂ 1 | 5 | 95 | >99 | 6 | 93 | >99 |
| (R)-α-Me-PG-NH₂ 2 | 8 | 92 | >99 | 6 | 94 | >99 |
| (R)-α-Et-PG-NH₂ 3 | 24 | 76 | >99 | 18 | 82 | 99 |
| (R,S )-α-Bn-PG-NH₂ 4 | 10 | 90 | >99 | 18 | 82 | 99 |
| (R,S )-α-H-PG-NH₂ 5 | 22 | 78 | >99 | 31 | 69 | 98 |
| (R,S )-α-Me-HHPG-NH₂ 6 | 17 | 84 | >99 | 29 | 71 | 99 |
| (R,S)-IVa-NH₂ 7 | 9 | 91 | >99 | 19 | 81 | >99 |
| (R,S)-α-Me-PG-OH 8 | 41 | 58 | 96 | 40 | 60 | 98 |

EXAMPLE XXIV

Conversion of (R,S)-1-phenylethanol Using Different Transfer Hydrogenation Catalysts The following procedure was performed using the precursor complexes and ligands mentioned in Example XXIII. Placed in a three-necked round bottom flask of 100 ml:

| | |
|---|---|
| Catalyst precursor: | 0.036 mmol |
| Ligand: | 0.072 mmol |

The complexation was carried out at 70° C. in 36 mmol (R,S)-1-phenylethanol. The clear solution was cooled to room temperature. To the obtained catalyst solution is respectively added:

| | |
|---|---|
| Isopropyl butyrate (130): | 72 mmol |
| o-xylene: | 23 ml |
| $K_2CO_3$ (138) | 2 g |
| Novozym435 ®: | 400 mg |

The resulting mixture was degassed by five vacuum (50 mbar)/nitrogen purge cycles. The reaction mixture was heated to 70° C. During the course of the reaction the pressure was slowly reduced to 80 mbar. Under the chosen conditions isopropanol and small amounts of o-xylene and isopropyl butyrate were destined during 22 hours.

Results:

TABLE

Conversion of (R,S)-1-phenylethanol after 22 h using different catalysts

| | Precursor | | | | |
|---|---|---|---|---|---|
| | [RuCl$_2$cymene]$_2$ | | | [IrCl$_2$Cp] | |
| | Yield (%) | | E. e. (%) | Yield (%) | E. e. (%) |
| Ligand | Alcohol | Ester | Ester | Alcohol | Ester | Ester |
| (R,S)-α-Me-PG-NH$_2$ 1 | 3 | 97 | >99 | 1 | 99 | >99 |
| (R)-α-Me-PG-NH$_2$ 2 | 6 | 94 | >99 | 2 | 98 | >99 |
| (R)-α-Et-PG-NH$_2$ 3 | 19 | 81 | >99 | 10 | 90 | >99 |
| (R,S) )-α-Bn-PG-NH$_2$ 4 | 6 | 94 | >99 | 6 | 94 | >99 |
| (R,S) )-α-H-PG-NH$_2$ 5 | 23 | 77 | >99 | 9 | 91 | >99 |
| (R,S) )-α-Me-HHPG-NH$_2$ 6 | 14 | 86 | >99 | 14 | 86 | >99 |
| (R,S)-IVa-NH$_2$ 7 | 8 | 92 | >99 | 3 | 97 | >99 |
| (R,S)-α-Me-PG-OH 8 | 38 | 61 | 97 | 44 | 55 | 96 |

EXAMPLE XXV

Conversion of (R,S)-1-phenylethanol to (R)-α-methylbenzyl Butyrate Using Catalysts Based on [RuCl$_2$cymene]$_2$ Additional ligands were used in the preparation of racemisation catalysts from [RuCl$_2$cymene]$_2$.

Ligands:

9. aminoethanol

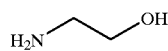

10. (R,S)-1-amino-2-propanol

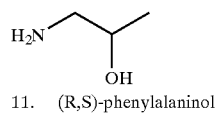

11. (R,S)-phenylalaninol

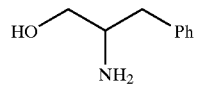

12. (R,S)-amino-2-phenyl-1-propanol

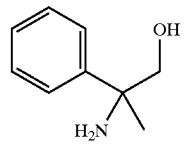

13. Rac. Cis-1-amino-2-indanol

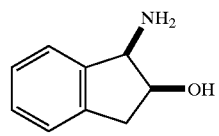

14. (+)-ephedrine ([1S,2R]-(+)-2-[methylamino]-1-phenylpropan-1-ol)

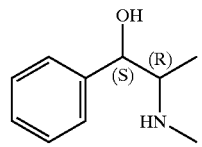

15. (R,S)-Valinamide

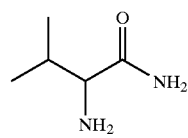

16. Mono-tosyl-ethylenediamine

16

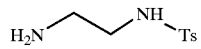

The following procedure was performed using ligands 9 to 16:

Placed in a three-necked round bottom flask of 100 ml:

[RuCl₂cymene]₂ (612,4)

| Ligand: | small excess compared to ruthenium |
|---|---|
| (R,S)-1-phenylethanol (122): | 36 mmol |

The catalyst precursor and the ligand were dissolved in the substrate. The resulting clear solution was degassed by five vacuum (50 mbar)/nitrogen purge cycles. The complexation was carried out at 70° C. at atmospheric pressure. The obtained clear solution was cooled to room temperature. To the solution is respectively added:

| Isopropyl butyrate (130): | 72 mmol |
|---|---|
| o-xylene: | 23 ml |
| K₂CO₃ (138) | 2.5 g |
| Novozym435 ®: | 400 mg |

The reaction vessel was closed under air atmosphere. After reducing the pressure to 50 mbar the reaction mixture was heated to 70° C. The pressure in the reaction vessel was allowed to equilibrate at this temperature. During the course of the reaction the pressure was slowly adjusted to 80 mbar. Under the chosen conditions isopropanol and small amounts of o-xylene and isopropyl butyrate were destined during 21 hours.

Results:

EXAMPLE XXVI

Conversion of (R,S)-1-phenylethanol to (R)-α-methylbenzyl Butyrate Using a Iridium Racemisation Catalyst The following procedure is performed using different amounts of the mentioned catalyst:

Placed in a three-necked round bottom flask of 100 ml:

[IrCl₂CP]₂ (796)

| Ligand 12 (151): | small excess compared to iridium |
|---|---|
| (R,S)-1-phenylethanol (122): | 36 mmol |

The catalyst precursor and the ligand were dissolved in the substrate. The resulting clear solution was degassed by five vacuum (50 mbar)/nitrogen purge cycles. The complexation was carried out at 70° C. at atmospheric pressure. The obtained clear solution was cooled to room temperature. To the solution is respectively added:

| Isopropyl butyrate (130): | 72 mmol |
|---|---|
| o-xylene: | 23 ml |
| K₂CO₃ (138) | 2.5 g |
| Novozym435 ®: | 400 mg |

The reaction vessel was closed under air atmosphere. After reducing the pressure to 50 mbar the reaction mixture was heated to 70° C. The pressure in the reaction vessel was allowed to equilibrate at this temperature. During the course of the reaction the pressure was slowly adjusted to 80 mbar. Under the chosen conditions isopropanol and small amounts of o-xylene and isopropyl butyrate were destined during 21 hours.

TABLE

| Conversion of (R,S)-1-phenylethanol after 21 h ||||||||||
|---|---|---|---|---|---|---|---|---|---|
| Catalyst loading ||||||||||
| | 0.2 mol % |||| 1 mol % ||||||
| | Yield (%) || E. e. (%) || Yield (%) || E. e. (%) ||
| Ligand | Keton | Alc. | Ester | Alc. | Ester | Keton | Alc. | Ester | Alc. | Ester |
| 9 | 3 | 34 | 63 | 96 | 96 | 9 | 10 | 81 | 64 | 99 |
| 10 | 2 | 38 | 60 | 96 | 97 | 8 | 15 | 77 | 61 | 99 |
| 11 | 2 | 39 | 59 | 96 | 97 | 7 | 17 | 76 | 53 | 99 |
| 12 | 3 | 37 | 60 | 95 | 97 | 8 | 18 | 75 | 35 | 99 |
| 13 | 2 | 39 | 59 | 94 | 97 | 7 | 19 | 75 | 40 | 99 |
| 14 | 3 | 34 | 63 | 94 | 97 | 10 | 15 | 75 | 42 | 99 |
| 15 | 2 | 40 | 58 | 95 | 96 | 4 | 24 | 72 | 78 | 98 |
| 16 | 2 | 44 | 54 | 97 | 94 | 4 | 36 | 60 | 92 | 97 |

Results:

TABLE

| Catalyst loading | Conversion of (R,S)-1-phenylethanol after 21 h | | | | |
|---|---|---|---|---|---|
| | Yield (%) | | | E. e. (%) | |
| (mol %) | Keton | Alc. | Ester | Alc. | Ester |
| 0.2 | 2 | 21 | 77 | 89 | 98 |
| 1 | 5 | <1 | 94 | 8 | >99 |

EXAMPLE XXVII
Conversion of (R,S)-2-octanol to (R)-2-octyl Butyrate

Ligands used were mentioned in example XXIII.
Placed in a three-necked round bottom flask of 100 ml:

| | | |
|---|---|---|
| Catalyst precurcor: | | 0.036 mmol |
| Ligand: | | 0.072 mmol |
| (R,S)-2-octanol (130): | | 36 mmol |

The catalyst precursor and the ligand were dissolved in the substrate. The resulting clear solution was degassed by five vacuum (50 mbar)/nitrogen purge cycles. The complexation was carried out at 70° C. at atmospheric pressure. The obtained clear solution was cooled to room temperature. To the solution is respectively added:

| | |
|---|---|
| Isopropyl butyrate (130): | 72 mmol |
| o-xylene: | 23 ml |
| $K_2CO_3$ (138) | 2.5 g |
| Novozym435 ®: | 100 mg |

The reaction vessel was closed under air atmosphere. The resulting mixture was degassed by five vacuum (50 mbar)/nitrogen purge cycles. The reaction mixture was heated to 70° C. During the course of the reaction the pressure was slowly reduced to 80 mbar.

Under the chosen conditions isopropanol and small amounts of o-xylene and isopropyl butyrate were destilled during 20 hours.

TABLE

| Conversion of (R,S)-2-octanol after 20 h using different catalysts | | | | | |
|---|---|---|---|---|---|
| | Precursor | | | | |
| | $[RuCl_2cymene]_2$ | | | $[IrCl_2Cp^*]$ | |
| | Yield (%) | | E. e. (%) | Yield (%) | E. e. (%) |
| Ligand | Alcohol | Ester | Ester | Alcohol | Ester | Ester |
| 1 | 6 | 94 | 96 | 5 | 95 | 91 |
| 7 | 16 | 84 | 90 | | | |

What is claimed is:

1. Process for the preparation of an enantiomerically enriched ester, which comprises subjecting a mixture of enantiomers of the corresponding secondary alcohol and an acyl donor, to an enantioselective conversion in the presence of a racemisation catalyst to form the corresponding ester and a residue of the acyl donor, and irreversibly removing the residue from the phase in which the enantioselective conversion takes place.

2. Process according to claim 1 in which the concentrations of secondary alcohol and acyl donor are higher than 1M.

3. Process according to claim 2 wherein said concentrations are higher than 2M.

4. Process according to claim 1 which is performed in the absence of solvent.

5. Process according to claim 1, wherein the enantioselective conversion is an enzymatic conversion.

6. Process according to claim 1, wherein the racemisation catalyst is a transfer hydrogenation catalyst.

7. Process according to claim 1, wherein the racemisation catalyst comprises Ru or Ir.

8. Process according to claim 7, wherein the racemisation catalyst contains an amino acid amide of the formula (1)

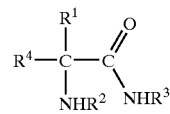

(1)

wherein $R^1$ and $R^4$ each independently represent H, an alkyl or a phenyl group;

$R^2$ and $R^3$ each independently represent H or an alkyl group; or $R^1$ and $R^2$ form a ring together with the N and C atoms to which they are bound.

9. Process according to claim 1, wherein the enantioselective conversion is performed in the presence of a ketone.

10. Process according to claim 1, wherein the secondary alcohol is generated in situ from the corresponding ketone in the presence of a hydrogen donor.

11. Process according to claim 10, wherein said generating is in the presence of a reducing agent.

12. Process according to claim 1, wherein residue of the acyl donor is converted in situ into another compound.

13. Process according to claim 1, in which the residue of the acyl donor is removed via distillation under reduced pressure.

14. Process according to claim 13, in which the acyl donor is a carboxylic acid ester of an alcohol (1–7C).

15. Process according to claim 14 wherein the acyl donor is the ester of an alcohol (1–4C) and a carboxylic acid (4–20C).

16. Process according to claim 1, which further comprises converting the enantiomerically enriched ester obtained into the corresponding enantiomerically enriched alcohol.

17. Process according to claim 16, in which the converting is in the presence of an enantioselective enzyme.

18. Process according to claim 1, which further comprises converting the enantiomerically enriched ester into a liquid crystal, an agrochemical or a pharmaceutical.

19. Process according to claim 16, which further comprises converting the enantiomerically enriched alcohol into a liquid crystal, an agrochemical or a pharmaceutical.

* * * * *